(12) United States Patent
Hallam et al.

(10) Patent No.: US 6,187,815 B1
(45) Date of Patent: Feb. 13, 2001

(54) METHODS AND COMPOSITIONS FOR THE PROMOTION OF HAIR GROWTH

(76) Inventors: Kenneth M. Hallam, 9609 Labrador La., Cockeysville, MD (US) 21030; Howard N. Robinson, 18 Hickory Knoll Ct., Lutherville, MD (US) 21093

(*) Notice: Under 35 U.S.C. 154(b), the term of this patent shall be extended for 1073 days.

(21) Appl. No.: 08/608,954

(22) Filed: Feb. 29, 1996

Related U.S. Application Data (63) Continuation of application No. 08/315,903, filed on Sep. 30, 1994, now abandoned, which is a continuation-in-part of application No. 07/837,222, filed on Feb. 18, 1992, now abandoned.

(51) Int. Cl.[7] .................. A61K 31/24; A61K 31/505; A61K 31/44
(52) U.S. Cl. .................. 514/535; 514/275; 514/356
(58) Field of Search .................. 514/275, 356, 514/535

(56) References Cited

U.S. PATENT DOCUMENTS 4,329,338 * 5/1982 Szego et al. .................. 424/180

* cited by examiner

Primary Examiner—Minna Moezie
Assistant Examiner—S. Wang
(74) Attorney, Agent, or Firm—Leonard Bloom (57) ABSTRACT

Compositions, medicaments, and methods for the promotion of hair growth are disclosed. These compositions and medicaments are comprised of either local anesthetics of the secondary or tertiary amino type or niacin. The preferred secondary and tertiary amino compounds include those which are esters of para-aminobenzoic acid, esters of benzoic acid, esters of meta-amino benzoic acid, amides, ethers, and ketones. The preferred compositions and medicaments include either procaine hydrochloride or niacin or procaine hydrochloride and niacin in a non-sulfur-containing carrier. The disclosed compositions and medicaments may be topically applied to a scalp in need thereof by an eyedropper or other suitable means. An improved embodiment of this application adds minoxidil.

4 Claims, 1 Drawing Sheet

FIG. 1

METHODS AND COMPOSITIONS FOR THE PROMOTION OF HAIR GROWTH

CROSS-REFERENCE TO RELATED APPLICATIONS

This application is a continuation of application Ser. No. 08/315,903, filed Sep. 30, 1994 now abandoned which is a continuation in part of application Ser. No. 07/837,222, filed Feb. 18, 1992, now abandoned entitled "Method and Compositions for the Promotion of Hair Growth".

FIELD OF THE INVENTION

The present invention is directed to methods and compositions for promoting the activity of the hair follicles of a living organism and, in particular, to compositions, medicaments, and methods for the treatment of the hair follicles of a human scalp to promote the growth of hair thereon.

BACKGROUND OF THE INVENTION

At birth, the average human scalp has approximately 100,000–150,000 hair follicles. Initially, hair follicles normally exhibit fine lanugo hair shafts, which are commonly referred to as "baby hair". This lanugo hair "matures" eventually, into terminal hair shafts, which is the hair most often exhibited during adolescence and adulthood. Thereafter, this terminal hair may remain as such, or it may develop into non-terminal vellus hair, which is commonly referred to as a "thinning" of the hair and, in more advanced stages, baldness.

The precise mechanism that triggers the development of non-terminal vellus hair is not precisely understood or agreed upon. However, there have been numerous attempts to provide an effective safe prophylaxis to arrest development of non-terminal vellus hairs and even to stimulate the regeneration of these vellus hairs into terminal hair shafts. Unfortunately, none of these attempts have proven to be fully satisfactory.

Thus, it can be seen that there remains a need for compositions, medicaments, and methods for administering the same, which are effective in stimulating the development of terminal hairs from non-terminal vellus hairs, are safe for use with a human host, and which are easy to administer.

There are many causes of hair loss for which suitable treatments are well known. For example, if the hair loss is due to general poor health of the patient, then a program designed to improve overall health would be instituted. If the patient's dietary habits are the cause of hair loss, then the patient's diet should be changed. If the patient's medications have the side effect of hair loss, then the medications should possible be changed. If a patient's shampoo is the cause of the hair loss, then the shampoo should be changed. If the patient's hair loss can be attributed to certain types of stress, then those types of stress should be eliminated or reduced. A patient's hair loss may be attributable to certain underlying dermatological conditions such as psoriasis, seborrheic dermatitis, perifolliculitis capitis, pseudopelade of Brocq (alopecia cicatricata), lichenplanopilaris, fungal and bacterial infections, connective tissue diseases such as lupus erythematosus, scleroderma, sarcoidosis, genetic abnormalities (including ectodermal dysplasia) among others.

A patient's hair loss may be attributable to certain underlying symptomatic conditions or drug exposure, such as telogen effluvium and anagen effluvium. The compositions and methods of the invention may be employed to supplement or augment known treatments for such conditions.

Telogen effluvium is hair loss that often results in three to six months after a serious illness such as pneumonia, a life-threatening illness, a surgical intervention, or other illness that requires a person to spend an unusually large amount of time in bed rest. Telogen effluvium generally self corrects from three to six months after its onset.

Anagen effluvium is hair loss that results when patients are administered chemotherapeutic agents, or other toxic agents. It is theorized that anagen effluvium is caused by a sudden shock to hair generating tissues (hair bulbs) in the growing state that can result from the administration of chemotherapeutic agents. As a result of the shock, the growing hairs fall out of the hair follicles.

If the patient's hair loss is due to hypothyroidism, then increased thyroid hormones can be administered. If perceived hair loss is due to hyperthyroidism, then the patient's thyroid activity can be reduced by drug therapy. It is noted that hypothyroidism diminishes the amount of hair that will grow because of decreased metabolic rates. Hyperthyroidism causes hairs to become very fine, and the very fine hairs are perceived to be hair loss.

To determine specific known causes of hair loss, a history is taken, and a physical examination is conducted. Once a known cause of hair loss is diagnosed for which a known treatment is accepted, then the known treatment can be instituted.

However, even with types of hair loss whose cause is determined and whose treatment is known, the rate of return of the lost hair may often be undesirably slow. It would be desirable, therefore, to be able to treat the patient being treated for a known cause of hair loss to accelerate the return of hair to such patients.

There are other types of hair loss for which the causes are less well understood, and only a few and limited known effective treatments are accepted in medical practice, i.e., the use of topical minoxidil. For these types of hair loss, the need for alternate effective treatments is very strong. Some examples of hair loss for which satisfactory treatments are not currently available include: male androgenetic alopecia and female androgenetic alopecia (male and female pattern baldness).

Another form of alopecia, known as alopecia areata (including alopecia totalis and alopecia universalis), is a type of hair loss for which no single or multiple treatment modalities (even including minoxidil) are considered to be highly effective.

As further background, it is noted that some vasodilators have been tried topically to treat hair loss, and these vasodilators have not been effective. For example, diazoxide has been tried topically on the scalp to promote hair growth, but this was not deemed to be effective.

It would be desirable to provide effective topical treatments of the hair loss conditions for which satisfactory topical treatments are not currently available.

A number of patents and publications have been uncovered which may be relevant to the scalp treatment methods and compositions of the invention set forth hereinbelow. These patents and publication are as follows, in approximate chronological order:

1. French patent No. 336,814 of Ascoli (1904)
2. New York State Journal of Medicine, Vol. 49, (1949), pages 1317–1318
3. Aslan A: Med. Klin.: 52, 1758, 1759, 1760 (1957)
4. Scholzel, P.: Med. Klin.: 53, 2239 (1958)
5. French patent No. 1439833 of Serviere (1966)

6. U.S. Pat. No. 3,644,364 of Anthony (1972)
7. Chemical Abstracts No. 79:23508s (1973)
8. French patent No. 72.39675 of Indaly Oy (1973)
9. UK patent No. 1 354 446 of Indal Oy (1974)
10. U.S. Pat. No. 3,896,238 of Smith (1975)
11. U.S. Pat. No. 3,903,256 of MacMillan et al (1975)
12. U.S. Pat. No. 3,952,099 of Smith (1976)
13. *Merck Index of Chemicals and Drugs*, hereinafter "Merck", 9th Edition, Merck & Co., Rahway, N.J., (1976), entries 6340 and 6343.
14. U.S. Pat. No. 4,139,619 of Chidsey (1979)
15. U.S. Pat. No. 4,150,114 of Smith (1979)
16. UK patent no. 1 603 639 of Haggar (1981)
17. Chemical Abstracts No. 96:74505x (1981)
18. *Current Therapy*, (1981), page 662
19. U.S. Pat. No. 4,329,338 of Szego et al (1982)
20. Japanese application no. 58-103310 of Yoshiya (1983)
21. Conn's *Current Therapy*, 1984, entry on "Alopecia", by Gonzalez et al, pages 599–603.
22. Chemical Abstracts No. 104:24067u (1985)
23. EPO Patent No. 0 158 090 of Roshdy (1985)
24. U.S. Pat. No. 4,596,812 of Chidsey et al (1986)
25. EPO application No. 0 188 793 of Gans et al (1986)
26. UK patent application No. 2 176 104A of Grollier (1986)
27. UK patent application No. 2 177 919A of Salim (1987)

More specifically, with respect to the references listed above, the following summaries of their disclosures are provided.

1. French patent No. 336,814 of Ascoli (1904) appears to disclose a composition used to promote hair growth. The composition appears to disclose the active ingredient to be the chlorhydrate of cocaine. The carrier appears to be a grease, such as vaseline, to form a pomade.
2. New York State Journal of Medicine, Vol. 49, (1949), pages 1317–1318, discloses a solution of niacin and procaine hydrochloride that is used for intravenous administration to treat a number of conditions listed in Table 1. The conditions listed include traumatic, degenerative, inflammatory, and miscellaneous conditions, none of which include hair loss. The composition was administered in an isotonic saline solution. There is a disclosure that niacin or nicotinic acid has a vasodilating effect, especially upon the capillary bed.
3. Aslan A, in Med. Klin.: 52, 1758, 1759, 1760 (1957), appears to disclose, as indicated in the translation of the Scholzel article referred to below, that procaine has been used in injection or intravenous therapy of old people resulting in better mental and physical performance abilities, increase in muscle strength, improvement of rigidity, and stimulation of hair growth in many cases of baldness.
4. Scholzel, P., in Med. Klin.: 53, 2239 (1958), in an English translation of the article in German, discloses the general content of the Aslan article mentioned above and goes on to disclose findings relating to a specific patient who, after 40 years of alopecia, showed hair growth after intravenous procaine therapy. There is also a disclosure that a person named Kohler, reported in 1957, the use of a combination of procaine with various vitamins in an apparently injectable composition ("Gerioptil pro injectione"). However, the specific use of effects of the Kohler compositions were not disclosed.
5. French patent No. 1439833 of Serviere (1966) appears to disclose a composition which contains a synergistic combination of the following ingredients: malic acid, procaine, and a soluble derivative of sulfapyridine. The composition is apparently applied topically to improve hair characteristics, but not necessarily hair growth.
6. U.S. Pat. No. 3,644,364 of Anthony (1972) discloses a process for preparing compounds which include minoxidil, an agent that may promote hair growth.
7. Chemical Abstracts No. 79:23508s (1973) discloses an abstract of a German patent (to Indal Oy) that discloses hair growth promoting characteristics. The disclosures in the German patent of Indal Oy appear to be similar to the disclosures in French patent no. 72.39675 of Indal Oy (1973) and UK patent no. 1 354 446 of Indal Oy (1974) mentioned below.
8. French patent No. 72.39675 of Indal Oy (1973) appears to disclose the compositions that are disclosed in UK patent no. 1 354 446 of Indal Oy (1974).
9. UK patent No. 1 354 446 of Indal Oy (1974) discloses a composition for promoting the growth of hair. The composition contains nicotinic acid and salicylic and/or benzoic acid dissolved in a carrier containing ethanol, urea, polyoxyethylene sorbitan-monopalmitate or monostearate, with the remainder being isopropyl myristate.
10. U.S. Pat. No. 3,896,238 of Smith (1975) discloses compositions for enhancing the penetration of pharmacologically active agents through skin comprising a sugar ester in combination with a sulfoxide or phosphine oxide. In Example VI, a topical anesthetic composition is disclosed for use in a spray can. The composition contains 1% benzocaine and 0.15% decyl methyl sulfoxide in a carrier comprised of approximately 50% ethanol and approximately 50% of a spray can propellant. There is a disclosure that the benzocaine can be replaced by an equivalent amount of procaine hydrochloride.
11. U.S. Pat. No. 3,903,256 of MacMillan et al (1975) discloses compositions for topical application to skin comprising a sunscreen in certain aliphatic sulfoxides which enhance the penetration of the sunscreens through the skin. Example IV discloses a topical local anesthetic comprised of procaine hydrochloride, nonyl methyl sulfoxide, and the balance water.
12. U.S. Pat. No. 3,952,099 of Smith (1976) is very similar in its disclosure to the above-mentioned U.S. Pat. No. 3,896,238 of Smith (1975).
13. *Merck Index of Chemicals and Drugs*, hereinafter "Merck", 9th Edition, Merck & Co., Rahway, N.J., (1976), entries 6340 and 6343.
   Entry 6340 is for nicotinamide.
   Entry 6343 is for nicotinic acid also known as niacin. Nicotinic acid is soluble in propylene glycol.
14. U.S. Pat. No. 4,139,619 of Chidsey (1979) discloses compositions which employ minoxidil in carriers to be applied topically to a scalp to promote hair growth.
15. U.S. Pat. No. 4,150,114 of Smith (1979) is very similar in its disclosure to the above-mentioned U.S. Pat. No. 3,896,238 of Smith (1975).

16. UK patent No. 1 603 639 of Haggar (1981) discloses a composition for application to the hair and scalp for use in stimulating hair growth in treating alopecia and excessive hair loss. The composition includes a hair conditioner (lotion or cream) and a vitamin solution which contains vitamins B1, B2, B6, A, D, nicotinamide, and ascorbic acid. It has been found particularly advantageous to use Oil of Rosemary in the vitamin solution. More specifically, in one preferred embodiment, Oil of Rosemary is included. In another preferred embodiment, Oil of Balsam is included. In addition, the carrier can be the conditioner LIFE-TEX (T.M.) produced by Wella, which has been found satisfactory. The carrier desirably promotes absorption into the scalp and is preferably an antiseptic type spirit which may be alcohol, isophane insulin, or other biologically acceptable volatile liquid. However, white iodine is the preferred carrier. Petroleum jelly or liquid paraffin may also be included. There is a statement that the composition for application to the hair and scalp includes a commercial hair conditioner and a vitamin solution which contains one or more of the disclosed vitamins.

17. Chemical Abstracts No. 96:74505x (1981) discloses an abstract of the UK Haggar patent discussed above.

18. *Current Therapy*, (1981), page 662, discloses, that in the case of alopecia areata, single patches frequently regrow spontaneously within a few months although the course is unpredictable (including the rare extension to alopecia totalis or alopecia universalis), and recurrences are common.

19. U.S. Pat. No. 4,329,338 of Szego et al (1982) discloses compositions for use as cosmetics. The compositions include a reaction product of nicotinic acid, a nicotinic acid salt, or a nicotinic acid halide and a polyhydroxy compound whose general formula is given in the Abstract. The active agents are disclosed as exerting beneficial effects for stimulating scalp or hair bulbs.

20. Japanese application No. 58-103310 of Yoshiya (1983), in an English language Abstract, discloses a composition for accelerating hair growth that includes ginger in an alcoholic carrier which includes methyl alcohol, ethyl alcohol, and other lower alcohols.

21. Conn's *Current Therapy*, 1984, entry on "Alopecia", by Gonzalez et al, pages 599–603, discloses a classification of causes of alopecia. Two main categories are nonscarring alopecia and scarring alopecia. Both the nonscarring alopecia and the scarring alopecia are subdivided into more specific conditions. See Table 1 on page 599.

22. Chemical Abstracts No. 104:24067u (1985) discloses hair preparations for the promotion of hair growth which include extracts of the Acanthopanax root bark, with or without peripheral circulation promoting substances which include nicotinic acid.

23. EPO Patent No. 0 158 090 of Roshdy (1985), written in the German language, appears to disclose compositions which contain vitamin C, vitamin A, vitamins of the B series, phospholipids, and unsaturated fatty acids. The compositions can be used in carriers that include alcohol or isopropyl alcohol. Other components of the compositions may include lecithin, amino acids, UV stabilizers, or antihistamines.

24. U.S. Pat. No. 4,596,812 of Chidsey et al (1986) discloses methods and compositions for treating male pattern alopecia. The compositions include the substance known as minoxidil. Minoxidil is disclosed as a vasodilator that functions to dilate the peripheral vascular system. Minoxidil compositions are applied topically to the scalp and are used in a carrier system which can include equal parts of ethyl alcohol and propylene glycol.

25. EPO application No. 0 188 793 of Gans et al (1986) discloses compositions containing minoxidil that include a carrier containing 70% alcohol, 20% water, and 10% propylene glycol. In this patent, an improvement comprises the inclusion of a hydroxy (lower alkyl) acrylate polymer to retard seepage of the minoxidil beyond the application site.

26. UK patent application No. 2 176 104A of Grollier (1986) discloses compositions for the treatment of hair and of the scalp to promote fresh hair growth. It is disclosed that compositions containing nicotinic acid or its esters, when applied to the scalp, have rubefacient and vasodilant activity. The specific compositions disclosed in this patent include the combination of certain water-soluble polyamides of the poly-beta-alanine type with nicotinic acid or its esters. As shown in Examples 1 and 4, for a hair-care lotion, the carrier includes ethyl alcohol and water.

27. UK patent application No. 2 177 919A of Salim (1987) discloses, in Example 9, a topical preparation to restore hair growth to areas of the human scalp suffering from hair loss. The preparation includes procaine, a physiologically acceptable, organic, in vivo sulphydryl group releasing agent, and castor oil.

The following conclusions can be made from a consideration of the prior art discussed above. Procaine has been used topically, in the presence of other active ingredients and in the presence of complex carrier ingredients, often including sulfur-containing carriers, to treat the scalp for hair growth. It is also clear from the prior art that neither procaine nor niacin, either alone or in combination with one another, has been used topically without other active ingredients and without a complex carrier system which often includes sulfur-containing carriers and non-hydrophilic ingredients.

Carriers containing sulfur-containing ingredients have their problems. For example, the safety and efficacy of dimethylsulfoxide (DMSO) has not been sufficiently established to for the U.S. Food and Drug Administration to permit its use in the United States.

Carriers containing non-hydrophilic ingredients may have the undesirable property of impeding or preventing penetration of the active, hair-bulb treating agents into the hair bulb from the surface of the skin when the active ingredient is applied topically.

SUMMARY OF THE INVENTION

Accordingly, it is a primary object of the present invention to alleviate the disadvantages and deficiencies of the prior art by providing compositions and medicaments that are effective for stimulating the development (growth) of terminal hairs from the hair bulb of non-terminal vellus hair follicles.

It is another primary object of the present invention to provide compositions and medicaments which may safely be used with a human host.

It is still another primary object of the present invention to provide methods for stimulating the development (growth) of terminal hairs from the hair bulb of non-terminal vellus hair follicles.

It is still yet another primary object of the present invention to provide methods of safely administering the compositions and medicaments to a human host.

It is a further object of the present invention to provide such compositions, medicaments, and methods for the administration thereof, which are easy to perform.

Another object of the present invention is to provide topical methods of treating scalp hair loss and to stimulate scalp hair growth by employing solutions containing simply procaine (or a derivative thereof) and/or niacin in a simple, water-miscible carrier.

Still another object of the invention is to provide a topically applied composition that includes an agent that will stimulate hair growth by stimulating the hair bulb and that also includes a non-sulfur-containing carrier.

Yet another object of the invention is to provide a topically applied composition that includes an agent that will stimulate hair growth by stimulating the hair bulb and that also contains a carrier that does not include a sulfur-containing ingredient.

Still another object of the invention is to provide a topically applied composition that includes an agent for stimulating hair growth by stimulating the hair bulb and that also contains a carrier that does not contain non-hydrophilic ingredients.

In accordance with the teachings of the present invention, there is disclosed the use of a secondary or a tertiary amino local anesthetic for the manufacture of a topical medicament for stimulating the growth of a hair bulb of a vellus hair follicle.

Preferably, the secondary or tertiary amino local anesthetic is either a secondary or tertiary amino ester of para-aminobenzoic acid, or a secondary or tertiary amino type ester of either benzoic acid or meta-aminobenzoic acid, or a secondary or tertiary amino type amide or a secondary or tertiary amino type ether, or a secondary or tertiary amino type ketone.

In further accordance with the teachings of the present invention, there is disclosed the use of niacin for the manufacture of a topical medicament for stimulating the growth of a hair bulb of a vellus hair follicle.

In another aspect of the present invention, methods are disclosed for the preparation of the medicaments described above for stimulating the growth of a hair bulb of a vellus hair follicle.

In yet another aspect of the present invention, methods are disclosed for stimulating the growth of a hair bulb for a vellus hair follicle that involves the topical administration of a therapeutic amount of the medicaments described above to a patient in need thereof.

In still further accordance with the teachings of the present invention, a composition for stimulating the growth of a hair bulb of a vellus hair follicle is disclosed. This composition includes either a secondary or tertiary amino local anesthetic or niacin as its active ingredient. This composition further includes a pharmaceutically-acceptable carrier.

Preferably, the carrier is a hydrophilic carrier that does not have a sulfur-based ingredient and that may be chosen from the group consisting of propylene glycol, absolute alcohol, and isopropyl alcohol. Alternatively, a combination of two or more of these carriers may be employed.

In another aspect of the present invention, there is disclosed a method for stimulating the growth of a hair bulb of a vellus hair follicle. This method includes, first, preparing a composition for stimulating the growth of a hair bulb of a vellus hair follicle which includes either niacin or a secondary or tertiary amino local anesthetic as its active ingredient, and a hydrophilic carrier; and second, topically applying the composition to a scalp having a vellus hair follicle in need thereof.

DETAILED DESCRIPTION OF THE PREFERRED EMBODIMENTS

Figure 1:
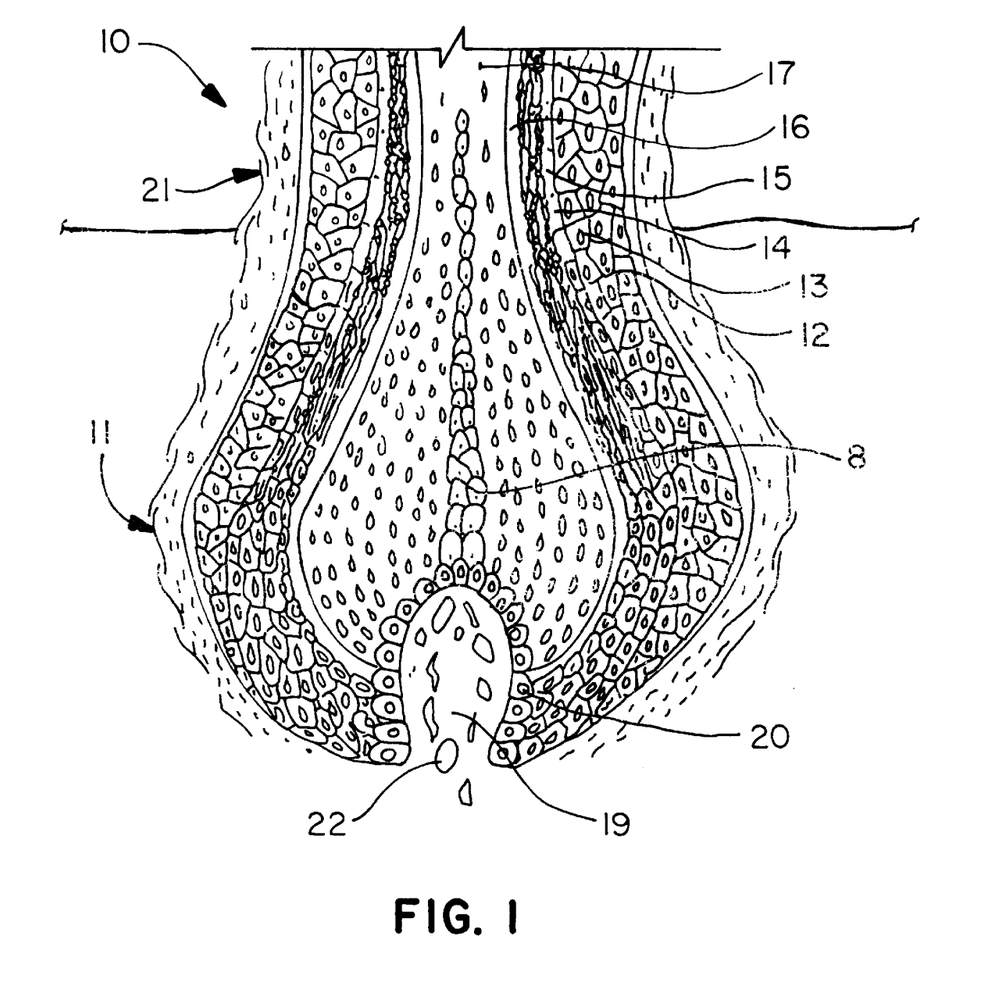
FIG. 1 illustrates, in cross-section, a healthy terminal hair follicle.

With reference now to FIG. 1, the hair follicle 10 includes a hair bulb 11 at the lower end thereof. The hair bulb 11 of the average mature hair follicle lies approximately 0.5–4 mm below the stratum corneum of the epidermis.

Generally, and as referred to herein, the hair follicle is comprised of seven layers: the outer root sheath 12; Henle's layer 13; Huxley's layer 14; cuticle of inner root sheath 15; the cuticle of hair shaft 16; the cortex of hair shaft 17; and the medulla of hair shaft 18. Further as referred to herein, the base of the hair follicle comprises a hair bulb 11 which surrounds a dermal papilla 19. Above the dermal papilla 19 is a germative cellular layer 20 which is the active growth portion of the hair shaft 21.

It is believed that the dermal papilla 19 receives nutrients and oxygen, etc. from the vascular superficial plexus 22 (which, as used herein, includes the superficial plexus and capillaries thereof) and carries these nutrients and oxygen to the growing portion 20 of the hair bulb 11. While not precisely understood or agreed upon, it is believed that growth of the hair shaft 21 (and hence, scalp hair) is a consequence of this interaction. It is our further belief that the presence of various androgens, such as testosterone, including dihydrotestosterone, can in certain genetically predisposed individuals, result in the development of non-terminal vellus hairs.

Also, while not precisely understood or agreed upon, the presence of these androgens is believed to be related to the presence in the hair bulb of various receptors which are sensitive therefor (which may or may not be genetically predetermined) and/or the presence of active androgens and their metabolites.

The compositions and medicaments (therapeutic compounds) of the present invention utilize a powerful vasodilator, especially one having strong local effects, as an active ingredient. Also, a pharmaceutically-acceptable hydrophilic carrier, devoid of a sulfur-containing ingredient, is utilized as an adjunct. The preferred active ingredient is either a secondary or tertiary amino local anesthetic or niacin.

The preferred secondary or tertiary amino local anesthetics (active ingredient) are the esters of para-aminobenzoic acid which include chloroprocaine, buthethamine, naepaine, and proparacaine. Especially preferred is procaine (which is also an ester of para-aminobenzoic acid) in the form of procaine hydrochloride (procaine HCl).

Alternatively, the preferred active ingredient may also be an amide including dibucaine, bupivacaine, lidocaine, mepivacaine, and prilocaine.

Other local anesthetics of the secondary or tertiary amino type which have applicability in the present invention as an active ingredient area; esters of benzoic acid such as cocaine, piperocaine, hexylcaine, meprylcaine, benoxinate, propoxycaine, and tetracaine; esters of meta-aminobenzoic acid, such as metabutethamine, isobucaine, and cyclomethycaine; ethers such as pramoxine and dimethisoguin; the ketone dyclonine; and the phenetidine derivative phenacaine.

If desired, niacin may also be added to the active ingredient enumerated above.

The preferred pharmaceutically-acceptable carrier of the compositions and medicaments of the present invention is propylene glycol. While not preferred, other carriers such as absolute alcohol (99% ethyl alcohol), and isopropyl alcohol may be employed either alternatively, or in combination therewith. Indeed, preferred compositions and medicaments are comprised of from 50% to 95% of propylene glycol and 15% to 30% of absolute alcohol. Other hydrophilic solutions, ointments, creams, or gels may also be employed.

One of the preferred compositions and medicaments useful in this practice is comprised of from 0.1–5% by weight of procaine hydrochloride (with 2% being preferred) in a carrier solution comprised of 50% to 95% by volume of propylene glycol (with 80% being preferred), 0.5 to 30% by volume ethyl (absolute) alcohol and 0.5 to 20% by volume of water (with 10% being preferred). These compositions and medicaments may be 0.1–5% by weight (with 2% being preferred) of procaine hydrochloride in carrier "vehicle N". Vehicle N is known as "Neutrogena Vehicle N" made by Neutrogena Dermatologics Division of Neutrogena Corporation, out of Los Angeles, Calif. 90045. Vehicle N as defined herein is a composition comprised of 47.5% by weight of ethyl alcohol, 4% by weight of isopropyl alcohol, 44% by weight of purified water, 0.5% by weight of Laureth-4 (a surfactant) and 4% by weight of propylene glycol.

It is possible that procaine is vasodilator that can have a prolonged action on hair bulbs. The procaine may be able to be applied only once a day because of its prolonged vasodilatory effects.

Variations of "vehicle N" that can be employed are as follows:

ethyl alcohol (in a range spanning 44.5%–51.0% by weight),

Laureth (in a range spanning 0.15–2.0% by weight), propylene glycol (in a range spanning 2.0%–6.0% by weight), isopropyl alcohol (in a range spanning 2.0%–6.0% by weight), and purified water (in a range spanning 40.0%–48.0% by weight).

It is noted that Laureth, which may be Laureth-4, is a surfactant. Alternate pharmaceutically-acceptable surfactants include ammonium lauryl sulfate, sodium lauryl sulfate, ammonium laureth sulfate, sodium myristate, sodium palmitate, among other pharmaceutically-acceptable surfactants.

Yet another preferred carrier is known as "Neutrogena Vehicle N (mild)" made by Neutrogena Dermatologics Division of Neutrogena Corporation, Los Angeles, Calif. 90045. This carrier approximately contains 41.5% by weight of ethyl alcohol, 6.0% by weight of isopropyl alcohol, 52.0% by weight of purified water, and 0.5% by weight of Laureth-4 (a surfactant).

Variations of "Vehicle N (mild)" that can be employed are as follows:

ethyl alcohol (in a range spanning 39.5%–43.50% by weight),

Laureth (in a range spanning 0.15–2.0% by weight), isopropyl alcohol (in a range spanning 47.0%–53.0% by weight), and purified water (in a range spanning 47.0%–53.0% by weight).

It is noted that Laureth, which may be Laureth-4, is a surfactant. Alternate pharmaceutically-acceptable surfactants include ammonium lauryl sulfate, sodium lauryl sulfate, ammonium laureth sulfate, sodium myristate, sodium palmitate, among pharmaceutically-acceptable surfactants.

If desired, niacin may also be added to the compositions and medicaments noted above. While the amount of niacin to be added may range from 0.01–5% by weight of the total composition or medicament, 0.1% is the preferred quantity.

Another of the preferred compositions and medicaments useful in this practice is comprised of a 0.01–5% by weight solution of niacin (with 0.1% being preferred) in a carrier solution comprised of 50 to 95% by volume of propylene glycol (with 80% being preferred), 0.5 to 30% by volume of ethyl (absolute) alcohol, and 0.5 to 20% by volume of water (with 10% being preferred). These compositions and medicaments may be comprised of from 0.01–5% (with 0.1% being preferred) of niacin in "vehicle N". Vehicle N as defined herein is a composition comprised of 47.5% by weight of ethyl alcohol, 4% by weight of isopropyl alcohol, 44% by weight of purified water, 0.5% by weight of Laureth-4 (a surfactant), and 4% by weight of propylene glycol.

The amount of niacin of the compositions and medicaments described above may range from 0.01–5% by weight of the total composition or medicament, with 0.1% of niacin being the preferred quantity.

These compositions and medicaments are topically applied directly to a scalp in need thereof by use of a dropper, a porous applicator, a roll top, small brush, or even by massaging in with the hands or any other means which is suitable for topical application which are well known to those skilled in the art. When a porous applicator is used, a microporous applicator is preferred, such as that provided in the package of Neutrogena Vehicle N, made by Neutrogena Dermatologics Division of Neutrogena Corporation, Los Angeles, Calif. 90045. The porous or microporous applicator is a filter designed to provide a controlled release of the drug to the surface of the skin. This filter utilizes a fine or ultra-fine porosity delivery system to provide a controlled release of the drug.

The precise amount of the compositions and medicaments to be applied is within the skill of the art to determine. However, the amount applied would be that quantity necessary to thinly saturate the affected area of the skin. In this regard, the application of from 1 to 3 cc of the compositions or medicaments will be preferable. These topical applications are preferably performed one to two times daily. The frequency of these applications may be increased to decreased, as needed, as would be obvious to one skilled in the art.

If desired, the compositions and medicaments may be incorporated in a shampoo or a gel form. In a shampoo, the compositions and medicaments include water, lauryl sulfate, a surfactant and, if desired, a fragrance. The shampoo is shaken prior to use to effect thorough mixing thereof and is hand-massaged into the scalp.

Compositions employed in carrying out the method of the invention will be more clearly perceived and better understood from the following specific examples.

In each example, unless otherwise indicated, the proportions presented for the active ingredients, such as niacin or procaine HCl, are on a weight % of active ingredient per unit volume of carrier ingredient basis (i.e., 5% procaine hydrochloride is 5 grams of procaine HCl per 100 cc of a pharmaceutically-acceptable topical carrier), and the proportions presented for the carrier consist of a percent by volume (i.e., 80% propylene glycol is 80 cc of propylene glycol per 100 cc of a pharmaceutically-acceptable topical carrier).

Example One

A 2% solution of procaine hydrochloride in a propylene glycol carrier is prepared. Approximately 1 to 3 cc of this composition or medicament is then placed in an eyedropper. The composition or medicament is then administered in a dropwise fashion on a portion of a human scalp in need thereof. Initially, these applications are made every twelve hours. Eventually, the frequency of these applications may thereafter be decreased (or increased) as needed.

Example Two

A 0.1% solution of niacin in a propylene glycol carrier is prepared. Approximately 1 to 3 cc of this composition or medicament is then placed in an eyedropper. The composition or medicament is then administered in a dropwise fashion on a portion of a human scalp in need thereof. Initially, these applications are made every twelve hours, Eventually, the frequency of these applications may thereafter be decreased (or increased) as needed.

Example Three

A 2% solution of procaine hydrochloride in a carrier solution of 50% to 95% propylene glycol and 15% to 30% of absolute alcohol is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Four

A 0.1% solution of niacin in a carrier solution of 50% to 95% propylene glycol and 15% to 30% of absolute alcohol is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually, the frequency of these applications may thereafter be decreased (or increased) as needed.

Example Five

A 2% by weight solution of procaine hydrochloride in a carrier solution of 47.5% by weight of ethyl alcohol, 4% by weight of isopropyl alcohol, 44% by weight purified water, 0.5% by weight of Laureth-4 (a surfactant) and 4% by weight of propylene glycol is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually, the frequency of these applications may thereafter be decreased (or increased) as needed.

Example Six

A 0.1% by weight solution of niacin in a carrier solution of 47.5% by weight of ethyl alcohol, 4% by weight of isopropyl alcohol, 44% by weight of purified water, 0.5% by weight of Laureth-4 (a surfactant) and 4% by weight of propylene glycol is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually, the frequency of these applications may thereafter be decreased (or increased) as needed.

Example Seven

A 2% solution of procaine hydrochloride in a carrier solution of 80% propylene glycol, 10% water and 10% ethyl (absolute) alcohol is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually, the frequency of these applications may thereafter be decreased (or increased) as needed.

Example Eight

A 0.1% solution of niacin in a carrier solution of 80% propylene glycol, 10% water and 10% ethyl (absolute) alcohol is prepared. Approximately 1 to 3 cc of this composition or medicament is then administered in a dropwise fashion on a portion of a human scalp in need thereof. Initially, the applications are made once every twelve hours. Eventually, the frequency of these applications may thereafter be decreased (or increased) as needed.

Example Nine

A 2% solution of procaine hydrochloride and 0.1% niacin in a propylene glycol carrier is prepared. Approximately 1 to 3 cc of this composition or medicament is then placed in an eyedropper. The composition or medicament is then administered in a dropwise fashion on a portion of a human scalp in need thereof. Initially, the applications are made once every twelve hours. Eventually the frequency of these applications may thereafter be decreased (or increased) as needed.

Example Ten

A 2% solution of procaine hydrochloride in a propylene glycol carrier is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Eleven

A 0.1% solution of niacin in a propylene glycol carrier is prepared. Approximately 1 to 3 cc of this composition or medicament is placed in a container having a microporous applicator. This composition or medicament is then administered by application through the microporous applicator so as to thinly saturate the afflicted area of the human scalp in need thereof. Initially, these applications are made every twelve hours. Eventually, the frequency of these applications may thereafter be decreased (or increased) as needed.

Example Twelve

A 2% solution of procaine hydrochloride in a carrier solution of 50% to 95% propylene glycol and 15% to 30% of absolute alcohol is prepared. Approximately 1 to 3 cc of this composition or medicament is placed in a container having a microporous applicator. This composition or medicament is then administered by application through the microporous applicator so as to thinly saturate the afflicted area of the human scalp in need thereof. Initially, these applications are made every twelve hours. Eventually, the frequency of these applications may thereafter be decreased (or increased) as needed.

Example Thirteen

A 0.1% solution of niacin in a carrier solution of 50% to 95% propylene glycol and 15% to 30% of absolute alcohol is prepared. Approximately 1 to 3 cc of this composition or medicament is placed in a container having a microporous applicator. This composition or medicament is then administered by application through the microporous applicator so as to thinly saturate the afflicted area of the human scalp in need thereof. Initially, these applications are made every twelve hours. Eventually, the frequency of these applications may thereafter be decreased (or increased) as needed.

Example Fourteen

A 2% solution of procaine hydrochloride in a carrier solution of 47.5% by weight of ethyl alcohol, 4% by weight of isopropyl alcohol, 44% by weight to purified water, 0.5% by weight of Laureth-4 (a surfactant) and 4% by weight of propylene glycol is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Fifteen

A 0.1% solution of niacin in a carrier solution of 47.5% by weight of ethyl alcohol, 4% by weight of isopropyl alcohol, 44% by weight of purified water, 0.5% of Laureth-4 (a surfactant) and 4% by weight of propylene glycol is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Sixteen

A 2% solution of procaine hydrochloride in a carrier solution of 80% propylene glycol, 10% water and 10% ethyl (absolute) alcohol is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Seventeen

A 0.1% solution of niacin in a carrier solution of 80% propylene glycol, 10% water and 10% ethyl (absolute) alcohol is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Eighteen

A 2% solution of procaine hydrochloride and 0.1% niacin in a propylene glycol carrier is prepared. Approximately 1 to 3 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Example Nineteen

A solution of 0.1% niacin and 2% procaine hydrochloride in a carrier solution of 50% to 95% propylene glycol and 15% to 30% of absolute alcohol is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty

A solution of 0.1% by weight of niacin and 2% by weight of procaine hydrochloride in a carrier solution of 47.5% by weight of ethyl alcohol, 4% by weight of isopropyl alcohol, 44% by weight of purified water, 0.5% Laureth-4 (a surfactant) and 4% by weight of propylene glycol is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty-One

A solution of 0.1% niacin and 2% procaine hydrochloride in a carrier solution of 80% propylene glycol, 10% water, and 10% ethyl (absolute) alcohol is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty-Two

A solution of 0.1% niacin and 2% procaine hydrochloride in a carrier solution of 50% to 95% propylene glycol and 15% to 30% of absolute alcohol is prepared. Approximately 1 to 3 cc of this composition or medicament is then placed in a container having a microporous applicator. The composition or medicament is then administered by application through the microporous applicator, so as to thinly saturate the afflicted area of the human scalp in need thereof. Initially, the applications are made once every twelve hours. Eventually, the frequency of these applications may thereafter be decreased (or increased) as needed.

Example Twenty-Three

A solution of 0.1% niacin and 2% procaine hydrochloride in a carrier solution of 47.5% by weight of ethyl alcohol, 4% by weight of isopropyl alcohol, 44% by weight of purified water, 0.5% by weight of Laureth-4 (a surfactant), and 4% by weight of propylene glycol is prepared. Approximately 1 to 3 cc of this composition or medicament is then placed in a container having a microporous applicator. The composition or medicament is then administered by application through the microporous applicator, so as to thinly saturate the afflicted area of the human scalp in need thereof. Initially, the applications are made once every twelve hours. Eventually, the frequency of these applications may thereafter be decreased (or increased) as needed.

Example Twenty-Four

A solution of 0.1% niacin and 2% procaine hydrochloride in a carrier solution of 80% propylene glycol, 10% water, and 10% ethyl (absolute) alcohol is prepared. Approximately 1 to 3 cc of this composition or medicament is then placed in a container having a microporous applicator. The composition or medicament is then administered by application through the microporous applicator, so as to thinly saturate the afflicted area of the human scalp in need thereof. Initially, the applications are made once every twelve hours. Eventually, the frequency of these applications may thereafter be decreased (or increased) as needed.

Example Twenty-Five

A 2.0% by weight solution of procaine hydrochloride in a carrier solution of 41.5% by weight of ethyl alcohol, 6.0% by weight of isopropyl alcohol, 50.0% by weight of purified water, and 0.5% by weight of Laureth-4 (a surfactant), is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty-Six

A 0.1% by weight solution of niacin in a carrier solution of 41.5% by weight of ethyl alcohol, 6.0% by weight of isopropyl alcohol, 51.9% by weight of purified water, and 0.5% by weight of Laureth-4 (a surfactant), is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty-Seven

A solution of 0.1% by weight of niacin and 2.0% by weight of procaine hydrochloride in a carrier solution of 41.5% by weight of ethyl alcohol, 6.0% by weight of isopropyl alcohol, 49.9% by weight of purified water, and 0.5% by weight of Laureth-4 (a surfactant), is prepared. Approximately 1 to 3 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example Twenty-Eight

A 2.0% by weight solution of procaine hydrochloride in a carrier solution of 41.5% by weight of ethyl alcohol, 6.0% by weight of isopropyl alcohol, 50.0% by weight of purified water, and 0.5% by weight of Laureth-4 (a surfactant), is prepared. Approximately 1 to 3 cc of this composition or medicament is then placed in a container having a microporous applicator. The composition or medicament is then administered by application through the microporous applicator so as to thinly saturate the afflicted area of the human scalp in need thereof. Initially, the applications are made once every twelve hours. Eventually, the frequency of these applications may thereafter be decreased (or increased) as needed.

Example Twenty-Nine

A 0.1% by weight solution of niacin in a carrier solution of 41.5% by weight of ethyl alcohol, 6.0% by weight of isopropyl alcohol, 51.9% by weight of purified water, and 0.5% by weight of Laureth-4 (a surfactant), is prepared. Approximately 1 to 3 cc of this composition or medicament is then placed in a container having a microporous applicator. The composition or medicament is then administered by application through the microporous application so as to thinly saturate the afflicted area of the human scalp in need thereof. Initially, the applications are made once every twelve hours. Eventually, the frequency of these applications may thereafter be decreased (or increased) as needed.

Example Thirty

A solution of 0.1% by weight of niacin and 2.0% by weight of procaine hydrochloride in a carrier solution of 41.5% by weight of ethyl alcohol, 6.0% by weight of isopropyl, 49.9% by weight of purified water, and 0.5% by weight of Laureth-4 (a surfactant), is prepared. Approximately 1 to 3 cc of this composition or medicament is then placed in a container having a microporous applicator. The composition or medicament is then administered by application through the microporous application so as to thinly saturate the afflicted area of the human scalp in need thereof. Initially, the applications are made once every twelve hours. Eventually, the frequency of these applications may thereafter be decreased (or increased) as needed.

Example Thirty-One

A 2% solution of procaine hydrochloride, 0.1% niacin and minoxidil 2% in a propylene glycol and alcohol carrier is prepared. Approximately 1 cc of this composition or medicament is placed in a container having a microporous applicator. This composition or medicament is then administered by application through the microporous applicator, so as to thinly saturate the afflicted area of the human scalp in need thereof. Initially, these applications are made every twelve hours. Eventually, the frequency of these applications may thereafter be decreased (or increased) as needed.

Having set forth, above, a number of examples of compositions and methods of administering the compositions, now follows a Protocol for clinically testing a number of compositions employed in the method of the invention for promoting hair growth.

Protocol for Initial Clinical Testing of Hair Growth Compositions

This protocol tests the efficacy of certain hair compositions for treating male pattern alopecia. The protocol utilizes the compositions in the amounts that are contemplated will be utilized in the field. The protocol contemplates a double blind prospective study, wherein the subjects, as well as the principal investigator, are blinded to their treatment agent.

Subjects

The subjects utilized in this study are healthy, early balding, males. Specifically, each of the subjects suffers from balding on the vertex of the scalp. This balding has appeared within the last three (3) to five (5) years.

All subjects are between eighteen (18) and thirty-five (35) years of age.

Between forty (40) and sixty (60) subjects are employed in the study.

Screen Phase One

In the initial screening phase, the medical history of each of the potential subjects is obtained with specific emphasis placed on allergies to anesthetics. Patients having any allergies whatsoever to Novocaine are disqualified. Also, any potential subject currently taking any drugs, especially any antihypertensive drugs, is disqualified. Finally, any potential subject that has any significant medical problem(s) is disqualified.

Screen Phase Two

In the second screening phase, the subjects are tested for sensitivity to the compounds that are utilized in the study. This is done by the use of Patch Tests that are placed on the back of each potential subject, covered and kept dry for forty-eight (48) hours. After this period, the patch test is removed for thirty (3) minutes and then read on a standardized scale from 0 to 3+. The patch test includes:

(a) vehicle; Vehicle/N* (a composition of 47.5% by weight of ethyl alcohol, 4% by weight of isopropyl alcohol, about 44% by weight of purified water, 0.5% Laureth-4, and about 4% by weight of propylene glycol);

(b) 5% by weight of procaine hydrochloride in 100 cc of vehicle; and (c) 0.1% by weight of niacin in 100 cc of vehicle.

Any potential subject exhibiting significant sensitivity to any of the above agents will be dropped from the study.

*Note: Vehicle/N is manufactured by Neutrogena Corporation, 5760 W. 96th Street, P.O. Box 45036, Los Angeles, Calif. 90045, Telephone 1-800-421-6857.

Structure of the Test Groups

The subjects are divided into four test groups comprised of between ten (10) and fifteen (15) individuals each.

Three (3) of the groups of subjects formed apply active drugs, in topical form, twice daily to affected areas of the scalp. One (1) group applied vehicle alone, twice daily to affected areas of the scalp.

Examples of Group Structures

Group A
 10–15 subjects apply 5% by weight of procaine hydrochloride in 100 cc of vehicle b.i.d. to affected areas of the scalp.

Group B
 10–15 subjects apply 0.1% by weight of niacin in 100 cc of vehicle b.i.d. to affected areas of the scalp.

Group C
 10–15 subjects apply 5% by weight of procaine hydrochloride and 0.1% by weight of niacin in 100 cc of vehicle b.i.d. to affected areas of the scalp.

Group D
 10–15 subjects apply vehicle b.i.d. alone to affected areas of the scalp.

The selection of these concentrations is primarily due to the prolonged vasodilatory effects of the concentrations.

All subjects, as well as the principal investigator, are blinded to their treatment agent. The study is a double-blind perspective study.

Testing

Subject Preparation

The same principal instructor instructs each subject as to exactly how, where, and when to apply the medication, Warnings are also given to each subject (before and at the initiation of the study) as to the possible side effects, including dizziness, flushing, nausea, and palpitations that may be expected to occur from the use of the medicaments. Subjects are instructed to report any side effects that they may experience at any time throughout the study. Any side effects deemed dangerous to the subject are grounds to remove the patient from the study, and are documented accordingly.

The dosage of composition that is typically applied is one (1) cc.

The compositions are applied topically twice daily, every twelve (12) hours. The duration of the study is nine (9) months.

The hair and scalp should be dry prior to each topical application. All agents are applied topically using a metered spray applicator device, or any other suitable device, capable of delivering one (1) full dose of 1.0 cc. This can include used of a calibrated dropper, porous applicator (microporous preferred), or a roll top applicator.

Subjects are instructed to wash hands afterwards and also to avoid inhaling spray mist during application. Should any agent come in contact with eyes, subjects are instructed to flush eyes immediately with water.

Hair sprays, creams, or tonic are avoided during the study, especially those containing oil or water. If any hair spray is used, it should not be applied until 4 hours following topical application of agent.

If hair spray or dressing of any type is used, hair and scalp should be washed and dried thoroughly prior to topical application of agent.

Methods of Data Accumulation

At the initiation of the study, each subject has macrophotography done of balding areas of the vertex of scalp. Hairs are counted in a designated 2-square centimeter surface area on the vertex of the scalp. Hairs are classified as either vellus or terminal.

Subjects are seen and examined, as described above, on day one (1), which is designated as the baseline. Thereafter, on a monthly basis, subjects are seen and examined (with appropriate macrophotography performed), as described above. The end of the study is designated as nine (9) months. It is preferred that all patients be seen by the same principal investigator throughout the study. At three (3) months, six (6) months, and nine (9) months, data is complied and compared in each group category.

Note

All drug concentrations stated in the above protocol are expressed as weight per unit volume (W/V) unless otherwise specified. 5.0% procaine Hydrochloride is prepared using 5 gms of procaine hydrochloride (anhydrous) per 100 cc of vehicle: 0.1% niacin is prepared using 0.1 gms niacin per 100 cc of vehicle.

The foregoing description of the invention has been presented for purposes of illustration and description. It is not intended to be exhaustive or to limit the invention to the precise form disclosed.

Moreover, the methods and compositions of the invention can be used to treat fur-bearing animals, such as mink, in order to promote fur (hair) growth.

A pilot study has been performed at the Johns Hopkins Medical Institutions. The study was performed to determine whether a formulation of procaine 5% and niacin 0.1% applied topically to the scalp of men between the ages of 18 and 35 years inclusive would be safe and to examine whether treatment with the above specified composition was effective for producing hair growth in the treated subjects.

Included in this study were male patients of the ages set forth above who were experiencing the onset of vertex balding within the preceding 3–5 years. These men were of good health, with no history of allergy to procaine hydrochloride or niacin and all had normal blood chemistry.

Twenty-six subjects initially underwent screening evaluation including history, allergy testing and physical examination. The subjects after having been screened were instructed to return for evaluation at one, three, five, seven and nine month intervals. Over the course of the experiment twelve patients dropped out (two due to allergy and ten due to lack of interest); and fourteen patients completed the experiment. Over the period of the tests none of the patients who completed the test experienced any significant adverse reaction to the treatment with procaine and niacin.

The assessment of hair growth was done as per protocol. Using anatomic landmarks to insure that the assessment site for hair growth was the same at various times throughout the study, a 1.5 cm in diameter area of hair on the vertex was clipped prior to the study and at 3, 5, 7, and 9 months. Hair counts of terminal and indeterminant hairs combined, and vellus hairs separately, were independently performed by the primary investigator and research coordinator. These counts were then averaged to come up with the number of terminal and indeterminant hairs and vellus hairs for each individual. The results to date, which include 14 subjects who have completed this study, indicate that the average percent change in terminal and indeterminant hairs within the designated vertex site was a 5% loss. The 95% confidence interval=[−22.0%, 12.0%]. Within this group of 14 subjects, 5 had an increase in the number of terminal hairs, and of these 5, the average increase was 30.2% (95% confidence interval=[11.5%, 48.9%]). Of the 9 subjects who had a decline in terminal and indeterminant hair counts, the average loss was 24.6% (95% confidence interval=[−34.5%, −14.7%]).

In summary, 26 subjects initially enrolled in this study of a 5% procaine and 0.1% niacin topical solution in the treatment of early androgenic alopecia. Of these initial 26 subjects, 2 developed an allergic contact dermatitis to the solution, both of whom reacted to procaine. Fourteen of the subjects completed the 9 month study and none of these subjects showed any significant changes in CBC, chemistries, or EKG. Six subjects did experience mild erythema and scale on the scalp which did not cause them to discontinue use of the study drug. Analyzing these 14 subjects who completed this study, the overall percent change in terminal hair growth within the 1.5 cm assessment site on the vertex of the scalp was a 5% loss with 95% confidence intervals overlapping zero. Subgroup analysis of those who had an increased number of hair revealed the 5 subjects with increased growth had an average of 30.2% increase in terminal hairs within the assessment site, and of the 9 subjects who lost terminal hairs within the assessment site, the average loss was 24.6%.

It can be said that this topical procaine and niacin formulation appears to be safe, with the only significant adverse side effect being that of allergic contact dermatitis developing in 7.7% of the 26 patients initially beginning the drug. Mild irritant dermatitis consisting of erythema and scale occurred in 23% of subjects initially enrolled. No systemic effects of the topical medication were noted when assessment was done using pre- and post-history and physical examination, CBC, chemistries, and EKG. With regard to the possible effect of this solution on hair growth in this group of subjects, as there are no controls, it was impossible to say whether an average loss of 5% of terminal hairs is a positive effect or no effect. It may have been that overall as a group, these individuals were in a active phase of hair loss, and had they not used the study medication, would have lost more than 5% of terminal hairs over the vertex area of assessment. Conversely, these subjects may have-been in a stable phase and not really actively losing hairs, in which case it would appear that the study medication did not have an effect. Clearly, no statements can be made regarding effectiveness of this drug given the fact that control subjects were not studied.

It is true that the lead experimenter of the pilot study concluded that no statements can be made regarding the effectiveness of the procaine and niacin treatment in view of the fact that control subjects were not studied. However, while the results of the above study were inconclusive, the inventors are heartened by fact that 5 subjects of the experimental group did show an increase of hair growth. When these 5 subjects are evaluated in terms of the total number of patients (26 patients) who started the experiment, the indication is that approximately 20% of the patients showed improved hair growth; and when these 5 subjects are evaluated in terms of the total number of patients who completed the test (14 patients), the indication is that approximately 35% of the patients showed improved hair growth.

These results are not to be viewed in isolation, but are to be viewed in the context of results obtained using Rogaine®, a product of the Upjohn Company. Rogaine® which is an FDA approved hair growth stimulant. The Physicians' Desk Reference (1994) page 2444, states (regarding Rogaine®/minoxidil) that based on the investigators' evaluation there was no statistically significant difference in terminal hair regrowth between the treatment group and controls. Eight percent (8%) of the patients using Rogaine® demonstrated moderate to dense terminal hair regrowth compared with 4% using the placebo. Most patients did not demonstrate cosmetically significant regrowth of hair, however 26% of the patients showed minimal terminal hair regrowth using Rogaine® compared with 16% using placebo, as assessed by the investigator. Based on patient self-evaluation 26% using Rogaine® demonstrated moderate to dense hair regrowth compared with 11% using placebo. Based on investigators' evaluation 39% of the patients achieved moderate to dense terminal hair by 12 months. Based on patients assessment 48% felt that they had achieved moderate to dense hair regrowth in 12 months.

It is quite evident in view of the findings listed above that Rogaine®, a drug approved by the FDA is far from a 100% effective treatment as a hair growth stimulant. Based on a statistical comparison with Rogaine®, applicants' hair growth stimulant does show significant hair growth.

Applicants assert that their disclosed hair growth stimulant while not 100% effective displays significant hair growth stimulation.

In an unique embodiment of this invention minoxidil can be incorporated into the hair growth stimulating composition of procaine and niacin. Rogaine® is a hair growth proprietary product containing minoxidil and manufactured by the Upjohn Company. Rogaine® contains 20 mg. of minoxidil per milliliter in an alcohol base (a 2% solution). In use Rogaine® is applied to the scalp in one milliliter dosages twice daily. Rogaine® can be applied by the use of a metered spray, extender spray or rub-on applicator, the dosage being 20 mg. of minoxidil in one milliliter of dosage solution.

With 20 mg. in one milliliter of minoxidil added as the auxiliary agent, the dosage concentration of 0.1–5% of procaine would be operative, with 2% being preferred; and the dosage range for niacin being 0.01–5%, with 0.1% being preferred. Vehicles containing acceptable surfactants (e.g., Laureth-4 and sodium lauryl sulfate), propylene glycol, ethyl alcohol and water could be used as solvent vehicles of the minoxidil, procaine and niacin composition.

The optimum amount of minoxidil added to procaine and niacin would be 20 mg. of minoxidil. However, an effective dosage of 1–5% minoxidil could be increased or decreased based on observed effect on hair growth.

Examples of compositions containing procaine, niacin and minoxidil.

Example A

A solution of 0.1% niacin, 2% procaine hydrochloride and minoxidil 2% in a carrier solution of 50% to 95% propylene glycol and 15% to 30% of absolute alcohol is prepared. Approximately 1 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

Example B

A solution of 0.1% by weight of niacin and 2% by weight of procaine hydrochloride and 2% by weight of minoxidil in a carrier solution of 47.5% by weight of ethyl alcohol, 4% by weight of isopropyl alcohol, 44% by weight of purified water, 0.5% Laureth-4 (a surfactant) and 4% by weight of propylene glycol is prepared. Approximately 1 cc of this composition or medicament is then placed in an eyedropper. The composition or medicament is then administered in a dropwise fashion in a portion of a human scalp in need thereof. Initially, the applications are made once every twelve hours. Eventually, the frequency of these applications may thereafter be decreased (or increased) as needed.

The dosages herein set forth are optimum ranges, however they may be increased or decreased based upon observed results by those skilled in the art.

Furthermore, obvious modifications or variations of the method of the invention are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method for stimulating hair growth on the scalp by topically applying to the scalp, effective amounts of a topical composition consisting essentially of 0.1–5% procaine and 0.01–5% niacin in a topical hydrophilic vehicle for said procaine and niacin.

2. A topical composition for stimulating hair growth on the scalp, the composition consisting essentially of a combination of niacin and procaine hydrochloride in a pharmaceutically acceptable carrier containing propylene glycol for penetrating the scalp and for carrying the niacin and procaine hydrochloride therewith.

3. The composition of claim 2, wherein the niacin ranges from 0.01 to 5% of the total composition, and the amount of procaine hydrochloride ranges from 0.1 to 5% of the total composition.

4. The composition of claim 2, wherein the pharmaceutically acceptable carrier further includes a carrier chosen among the group consisting of lanolin, butyl alcohol, absolute alcohol, isopropyl alcohol and dimethyl sulfoxide, or a combination of two or more of these carriers.

* * * * *